US012678586B1

(12) United States Patent (10) Patent No.: US 12,678,586 B1

Brundage (45) Date of Patent: Jul. 14, 2026

(54) NOISE INJURY RELIEF SYSTEM

(71) Applicant: John Brundage, Laurel, MD (US)

(72) Inventor: John Brundage, Laurel, MD (US)

( * ) Notice: Subject to any disclaimer, the term of this patent is extended or adjusted under 35 U.S.C. 154(b) by 445 days.

(21) Appl. No.: 18/208,346

(22) Filed: Jun. 12, 2023

(51) Int. Cl.
*A61M 21/00* (2006.01)

(52) U.S. Cl.
CPC ..... *A61M 21/00* (2013.01); *A61M 2021/0027* (2013.01)

(58) Field of Classification Search
None
See application file for complete search history.

(56) References Cited

U.S. PATENT DOCUMENTS

| | | | |
|---|---|---|---|
| 4,325,386 | A | 4/1982 | Kratz |
| 2006/0129206 | A1 | 6/2006 | Merfeld et al. |
| 2007/0060948 | A1 | 3/2007 | Franz et al. |
| 2015/0066126 | A1 | 3/2015 | Marx et al. |
| 2016/0067099 | A1 | 3/2016 | Hayashi |
| 2019/0240174 | A1 | 8/2019 | During |
| 2020/0016070 | A1 | 1/2020 | Franz |
| 2022/0363742 | A1 | 11/2022 | de Juan et al. |

OTHER PUBLICATIONS

Teutsch, H. (Oct. 28, 2016). Audio and acoustic signal processing's major impact on smartphones. IEEE Signal Processing Society. https://signalprocessingsociety.org/publications-resources/blog/audio-and-acoustic-signal-processing%E2%80%99s-major-impact-smartphones (Year: 2016).*
Jupiter Io 4 Cellular Vaping system. Vaporcade Jupiter IO 4. (Aug. 7, 2018). https://store.vaporcade.com/collections/jupiter (Year: 2018).*
Google. (Oct. 1, 2020). Charge control—apps on Google Play. Google. https://play.google.com/store/apps/details?id=com.rhs.ccontrol &hl=en_US (Year: 2020).*
Silver luxury brushed metal aluminum Chrome Hard Case. BrainyDeal. (Feb. 4, 2020). https://brainydeal.com/products/silver-luxury-brushed-metal-aluminum-chrome-hard-case-for-iphone-5 (Year: 2020).*

(Continued)

*Primary Examiner* — Charles A Marmor, II
*Assistant Examiner* — Marc D. Honrath
(74) *Attorney, Agent, or Firm* — Cramer Patent & Design, PLLC.; Aaron R. Cramer

(57) ABSTRACT

A noise injury relief system is provided in the form of a portable handheld device configured for private therapeutic audio playback. The device includes an enclosure sized for pocket carry and having a front face with user controls and a cartridge insertion opening configured to receive a vaping cartridge. The front face includes an eleven-position slide switch for independently selecting internally stored recordings corresponding to eleven bells and a twelve-position slide switch positioned adjacent thereto for independently selecting twelve musical notes. An additional switch permits selection among different musical instruments for playback of the musical notes, and a volume control knob enables user adjustment of audio output. Internal audio signals are processed through a signal generator and transmitted wirelessly to a user audio device for private playback. The system is powered by an internal power supply and is configured for repeated use.

2 Claims, 4 Drawing Sheets

(56)  References Cited

OTHER PUBLICATIONS

Phones with Micro SD Slot. BestBuy.com. (Apr. 24, 2022). https://www.bestbuy.com/site/shop/phones-with-micro-sd-card-slot (Year: 2022).*

All Vape cartridges (Prescription Medical Cannabis). MedBud UK. (Feb. 4, 2023). https://medbud.wiki/vape-cartridges/ (Year: 2023).*

IPhone Vaporizer Case. ThisIsWhyImBroke. (Jun. 28, 2023). https://www.thisiswhyimbroke.com/iphone-vaporizer-case/ (Year: 2023).*

Mixing station. Mixing Station. (Jun. 8, 2023). https://mixingstation.app/ (Year: 2023).*

Plastic Cell Phone Cases. BestBuy.com. (May 28, 2023). https://www.bestbuy.com/site/shop/plastic-mobile-phone-cases (Year: 2023).*

Smartphone Bluetooth Remote Audio Volume Controller—(andorid/IOS). TinySine. (Mar. 14, 2023). https://www.tinyosshop.com/tsa1110-smartphone-bluetooth-remote-audio-volume-controller (Year: 2023).*

Ruddock, D. (Jan. 19, 2024). What is a single-board computer (SBC)?. Esper. https://www.esper.io/blog/what-is-a-single-board-computer-sbc (Year: 2024).*

Your visit to Cologne Cathedral. Information Page [online]. Kölner Dom [retrieved on Nov. 28, 2022]. Retrieved form the Internet: <URL: https://www.koelner-dom.de/en>.

\* cited by examiner

NOISE INJURY RELIEF SYSTEM

RELATED APPLICATIONS

None.

FIELD OF THE INVENTION

The present invention relates to a system and corresponding device that relieves and or reduces injuries, specifically post-traumatic stress disorder (PTSD), related to noise.

BACKGROUND OF THE INVENTION

There are numerous individuals who suffer from post-traumatic stress disorder (PTSD), which can often be associated with vestibular disorders originally triggered by intense auditory stimuli like close-range gunshots or explosions. Such vestibular disorders can arise from various sources such as wartime experiences, natural disasters, illnesses, injuries, or criminal incidents.

While some people find relief from these symptoms by utilizing loud controlled continuous tones, such as those produced by tolling church bells, in combination with medical *Cannabis*, the necessary materials and equipment for such treatment are not conveniently portable or readily accessible outside of one's home environment. Moreover, the sound of the bells or tones can prove bothersome to individuals in close proximity.

Hence, there is a clear need for a solution that enables individuals to address the effects of vestibular disorders causing PTSD through sound therapy and medical *Cannabis* in almost any location and at any time. The development of the Noise Injury Relief System effectively meets this requirement by offering a comprehensive solution in a manner that is efficacious and cost-effective.

SUMMARY OF THE INVENTION

Embodiments of the present disclosure may include a noise injury relief system, including an enclosure having a plurality of rounded corners. Embodiments may also include a front face having a colored surface and a logo area with an indicia. Embodiments may also include a cartridge insertion opening disposed on top of the front face that accepts a standard vaping cartridge. Embodiments may also include a main controller. Embodiments may also include a radio module having an internal antenna.

In some embodiments, the enclosure may be constructed of brushed chrome metal. In some embodiments, the enclosure may be constructed of plastic material. In some embodiments, the front face includes an eleven-way slide switch that allows for audio play back of internally stored recordings of the eleven bells of the Kolner Dom in an independent manner.

In some embodiments, the front face includes a twelve-way slide switch that may be provided adjacent to the eleven-way slide switch to allow for play back of twelve musical notes in an independent manner. In some embodiments, the noise injury relief system, according to may include a first internal audio storage module and a second internal audio storage module for storage of sound patterns associated with the eleven bells of the Kolner Dom, as controlled by the eleven-way slide switch, and the twelve musical notes, as controlled by the twelve-way slide switch, respectively.

In some embodiments, the hi-fidelity signal generator ensures tonal reproduction of audio files stored in the first internal storage module and the second internal storage module. In some embodiments, the vaping cartridge may be filled with a *Cannabis* material. In some embodiments, the *Cannabis* material may be a medical *Cannabis* material.

In some embodiments, the noise injury relief system, according to may include a radio activation switch disposed on the front facing to allow for control of an internal radio. In some embodiments, the noise injury relief system, according to may include a switch disposed on the front facing to allow for selection of different musical instruments.

In some embodiments, the noise injury relief system, according to may include a volume control knob disposed on the front facing located immediately above the radio activation switch. In some embodiments, the noise injury relief system, according to may include a power supply providing electrical power for the noise injury relief system.

In some embodiments, the power supply includes a recharging system, recharging power may be provided by a USB charging port disposed on the enclosure. In some embodiments, the power supply may be selected from the group consisting of an on-board power source, a removable power source, a plurality of rechargeable batteries, or a plurality of removable batteries, or a plurality of battery packs.

In some embodiments, the noise injury relief system, according to may include a charge controller disposed on the front facing to ensure proper charging of the power supply and prevent overcharging. In some embodiments, the charge controller provides a regulated charge to the power supply while simultaneously providing operating current to the main controller.

In some embodiments, the noise injury relief system, according to may include an audio output passed to a hi-fidelity signal generator before being sent to a transmitter. In some embodiments, the transmitter may be a Bluetooth transmitter. In some embodiments, the main controller may be a single board computer.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
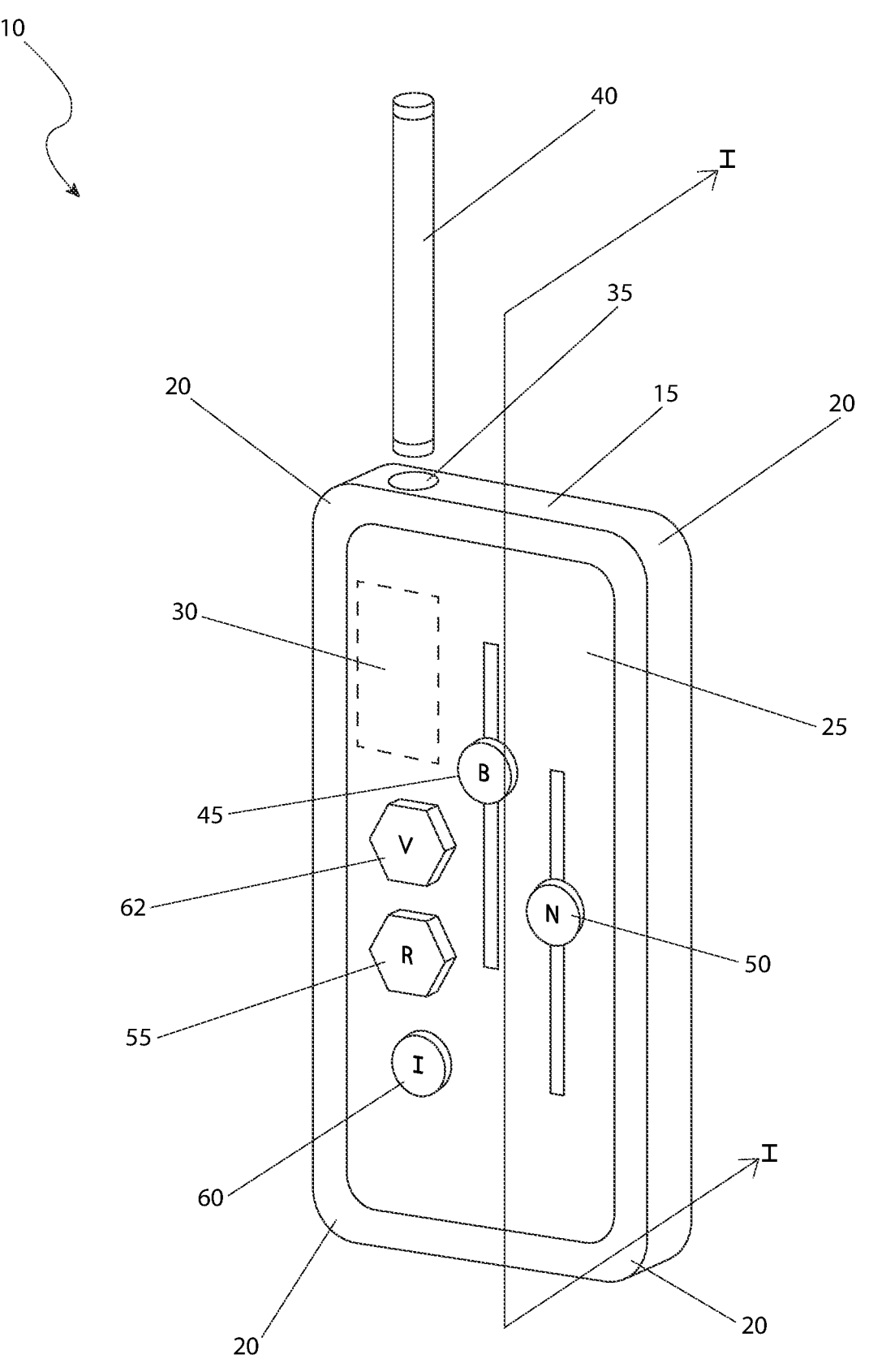
FIG. 1 is a perspective view of the noise injury relief system, according to the preferred embodiment of the present invention.

DESCRIPTIVE KEY 10 noise injury relief system
15 enclosure
20 rounded corner
25 front face 30 logo area
35 cartridge insertion opening
40 vaping cartridge
45 eleven-way slide switch
50 twelve-way slide switch
55 radio activation switch
60 switch
62 volume control
65 vaping cartridge compartment
70 power supply
75 USB charging port
80 charge controller
85 main controller
90 radio module
95 internal antenna
100 first internal audio storage module
105 second internal audio storage module
107 hi-fidelity signal generator
110 transmitter
115 wireless signal

DESCRIPTION OF THE PREFERRED EMBODIMENTS

The best mode for carrying out the invention is presented in terms of its preferred embodiment, herein depicted within FIGS. 1 through 4. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

1. Detailed Description of the Figures

Referring now to FIG. 1, a perspective view of the noise injury relief system 10, according to the preferred embodiment of the present invention is disclosed. The noise injury relief system (herein also described as the "system") 10, is a physiological device that is designed to reduce the effects of post-traumatic stress syndrome (PTSD) as a result of high or repeated noise levels. Such PTSD can create, or be the product of, traumatic brain injury (TBI). The features of the system 10 allow for control and even remission of vestibular disorders. The system 10 is provided with an enclosure 15 with the approximate dimensions of two and one-half inches (2½ in.) wide, five inches (5 in.) tall, and three-eighths of an inch (⅜ in.) thick. The enclosure 15 is provided with rounded corners 20 to facilitate insertion, removal and carrying in a clothing pocket. The enclosure 15 is preferably constructed of a brushed chrome metal or plastic material. The front face 25 may be provided with a colored surface such as red, blue, yellow, green, or black. A similar color may be provided on the rear surface (not shown). Additionally, the front face 25 is provided with a logo area 30 for purposes of various indicia such as product names, models, or the like. The top of the front face 25 is a cartridge insertion opening 35 that accepts a standard vaping cartridge 40, supplied by the user of the system 10. It is envisioned that the vaping cartridge 40 would be filled with a *Cannabis* material such as Jack Herer© Medical *Cannabis*, or the like. Further details on the usage of the vaping cartridge 40 will be described in greater detail herein below.

The front face 25 is provided with an eleven-way slide switch 45 that allows for the audio play back of internally-stored recordings of the eleven (11) bells of the Kolner Dom (Cologne Cathedral) in an independent manner. A twelve-way slide switch 50 is provided adjacent to the eleven-way slide switch 45 to allow for play back of twelve (12) musical notes in an independent manner. A radio activation switch 55 is provided to allow for control of an internal radio. A switch 60 is provided to allow for selection of different musical instruments that will play the twelve (12) notes provided above as selected by the twelve (12) way slide switch 50. A volume control 62 knob is located immediately above the radio activation switch 55. Further description and functionality of the eleven-way slide switch 45, the twelve-way slide switch 50, the radio activation switch 55, the switch 60, and the volume control 62, will be provided herein below.

Figure 2:
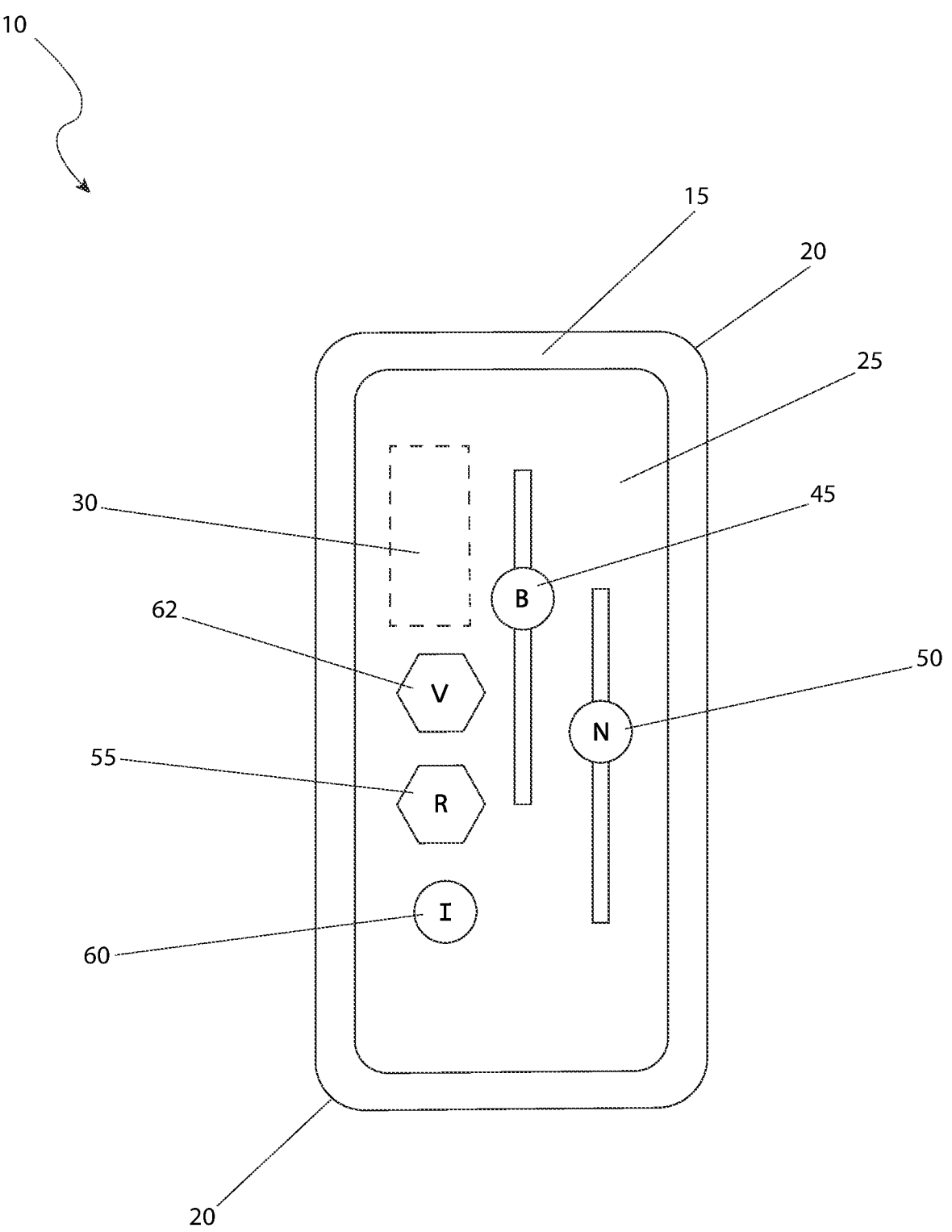
FIG. 2 is a front view of the noise injury relief system, according to the preferred embodiment of the present invention.

Referring next to FIG. 2, a front view of the system 10, according to the preferred embodiment of the present invention is depicted. This view provides further clarification on the outer enclosure 15 with the rounded corners 20. The front face 25 then contains the logo area 30, the eleven-way slide switch 45, the twelve-way slide switch 50, the radio activation switch 55, the switch 60, and the volume control 62, as aforementioned described.

Figure 3:
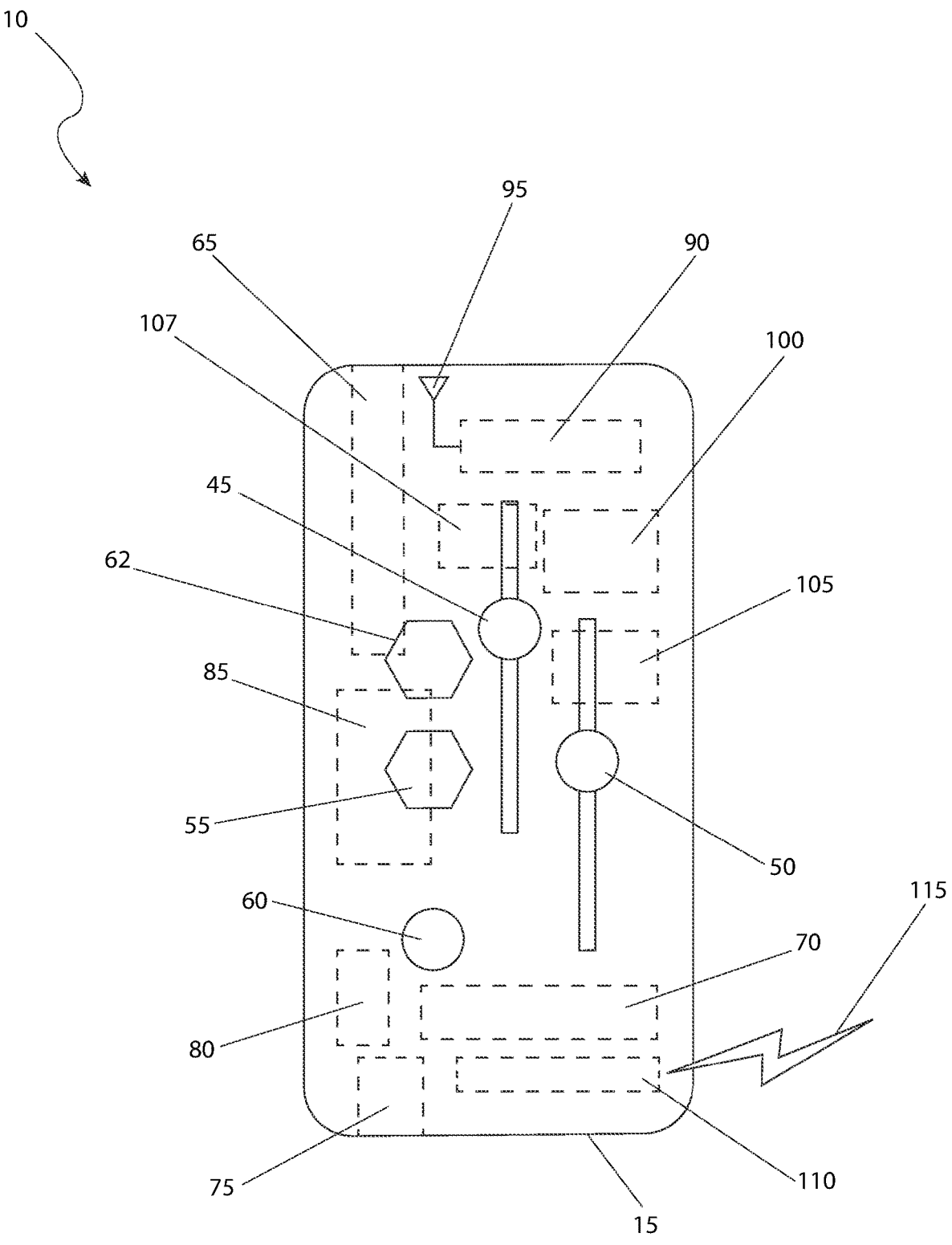
FIG. 3 is a sectional view of the noise injury relief system, as seen along a Line I-I, as shown in FIG. 1, according to the preferred embodiment of the present invention.

Referring now to FIG. 3, a sectional view of the system 10, as seen along a Line I-I, as shown in FIG. 1, according to the preferred embodiment of the present invention is shown. In addition to the eleven-way slide switch 45, the twelve-way slide switch 50, the radio activation switch 55, the switch 60, and the volume control 62, multiple other interior components are provided. Electrical power for the system 10 is provided by a power supply 70. Embodiments for the power supply 70 may comprise an on-board or removable power source, such as rechargeable batteries or removable batteries or battery packs. When the power supply 70 embodies a recharging system, recharging power is provided by a USB charging port 75 located in the bottom surface of the enclosure 15. A charge controller 80 is provided to ensure proper charging of the power supply 70 and prevent overcharging. The operation of the system 10 is provided by a main controller 85 such as a single board computer (SBC). The use of any specific type of main controller 85 is not intended as a limiting factor of the present invention.

A radio module 90, complete with an internal antenna 95, is provided for reception of radio signals. A first internal audio storage module 100 and a second internal audio storage module 105 is provided for storage of sound patterns associated with the eleven (11) bells of the Kolner Dom (Cologne Cathedral), as controlled by the eleven-way slide switch 45, and the twelve (12) musical notes, as controlled by the twelve-way slide switch 50, respectively. Audio output from the system 10 is passed to a hi-fidelity signal generator 107 before being sent to a transmitter 110, such as a Bluetooth® transmitter. The hi-fidelity signal generator 107 ensures the highest quality tonal reproduction of audio files stored in the first internal storage module 100 and the second internal storage module 105. The transmitter 110 produces a wireless signal 115 which pairs with a Bluetooth® device such as wireless headphones of the user's choosing for private, yet high-fidelity playback at a desired volume level as controlled by the volume control 62, such as a loud volume level.

Figure 4:
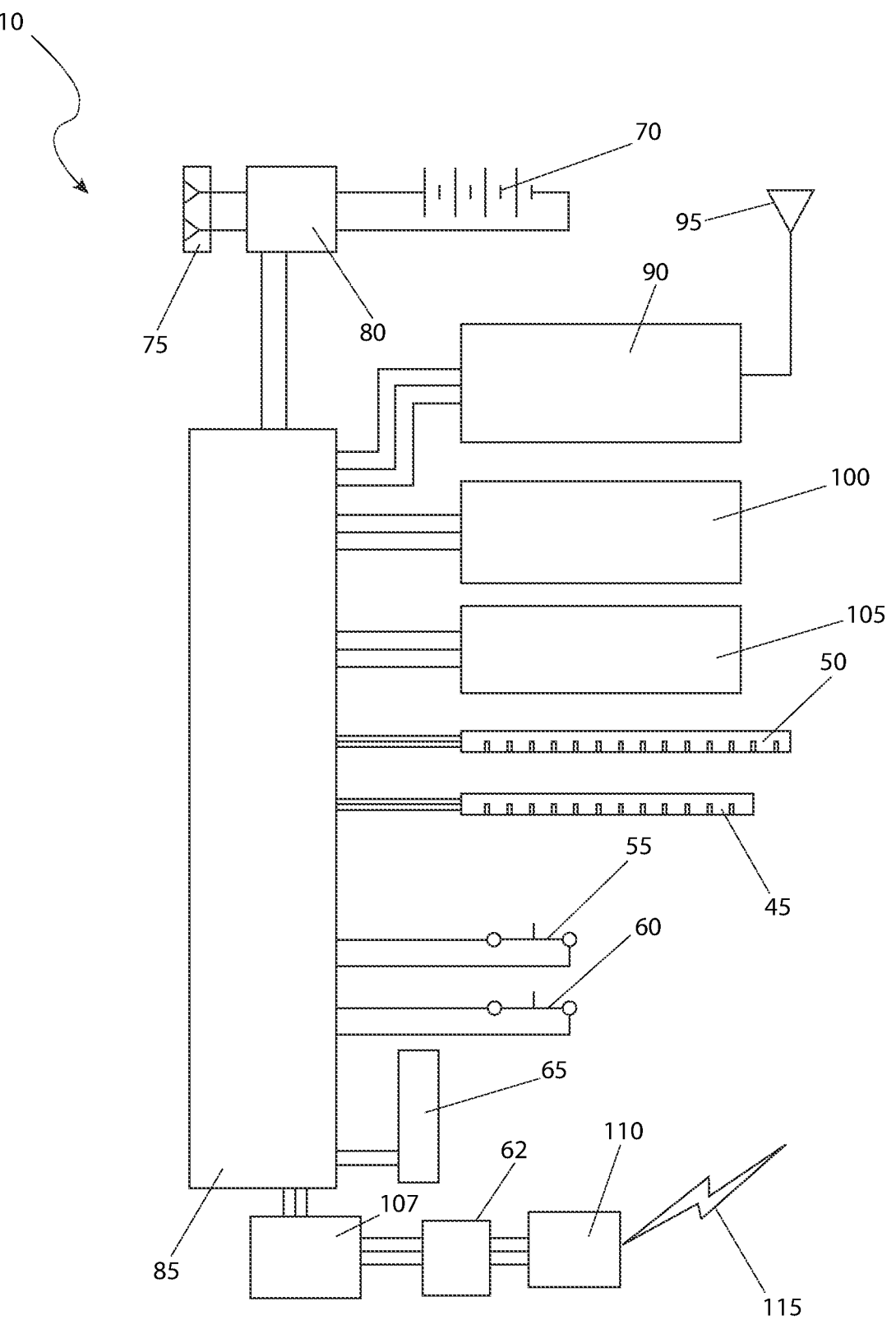
FIG. 4 is an electrical block diagram of the noise injury relief system, according to the preferred embodiment of the present invention.

Referring to FIG. 4, an electrical block diagram of the system 10, according to the preferred embodiment of the present invention is disclosed. When the power supply 70 is a recharging system, the USB charging port 75 provides electrical power to the charge controller 80 as aforementioned described. In turn, the charge controller 80 provides a regulated charge to the power supply 70 while simultaneously providing operating current to the main controller 85. The main controller 85 receives input commands from the eleven-way slide switch 45, the twelve-way slide switch 50, the radio activation switch 55, and the switch 60 along with referenced audio input signals from the radio module 90, the first internal audio storage module 100 and the second internal audio storage module 105. When the power supply 70 are replaceable batteries, it is ensured that batteries are properly in electrical and/or mechanical communication with the power supply 70.

Output signals are then provided for the operation of the vaping cartridge compartment 65 which contains the vaping cartridge 40 (as provided by the final user as shown in FIG. 1) and the audio output which passes through the hi-fidelity signal generator 107 and the volume control 62 before being sent to the transmitter 110 which is emitted from the system 10 as the wireless signal 115. All operating functionality of the system 10 including safety and inter-operational interlocks are provided by internal programmed logic contained within the main controller 85. Operation and usage of the system 10 will be as described below.

2. Operation of the Preferred Embodiment

The preferred embodiment of the present invention can be utilized by the common user in a simple and effortless manner with little or no training. It is envisioned that the system 10 would be constructed in general accordance with FIG. 1 through FIG. 4. The user would procure the system 10 from conventional procurement channels such as medical supply houses, marijuana supply shops, discount stores, drug stores, mail order and internet supply houses and the like. Special attention would be paid to the desired color of the front face 25, any provided indicia on the logo area 30, and the like.

After procurement and prior to utilization, the power supply 70 would be initially charged by applying electrical power to the USB charging port 75 for a period of time until properly charged when using a recharging means or by supplying replaceable batteries in electrical communication with the power supply 70. Periodic recharging at any point in time may be required as with any portable electronic device. At this point in time, the system 10 is ready of use.

During utilization of the noise injury relief system 10, for a given total time period of approximately two months (2 mos.) or sixty days (60 d.), the user would consume the contents of a vaping cartridge 40 on a nightly recurring basis utilizing the vaping cartridge compartment 65 of the system 10 on an exclusive basis. Over this given total time period, the contents of the vaping cartridge 40 will build up in the user's physiological system leading to improved results with the following usage of the system 10.

To eliminate or reduce the effects of various vestibular disorders including Meniere's disease, Superior canal dehiscence (SCD), vestibular fibrosis, the user would place an audio device of their choosing on their ears. The user would select the first setting on the eleven-way slide switch 45, which provides for the audio playback of the ringing of the Consecration Bell (Wandlungslocke) from the Kolner Dom (Cologne Cathedral) which is played for approximately twenty seconds (20 s.). The user would sit and relax for approximately twenty minutes (20 mins.). Any possible side effects experienced by the user may include pressure on the brain and the sensation of very low level of brain tissue electrical charges. This is then followed by experiencing improved balance, reduced dizziness, a lessening of nausea, lack of brain fog, increased energy, and an enhanced ability to concentrate. Ringing in the ears such as tinnitus may also be reduced.

Should the desired above-described reliefs and effects not be achieved at this point in time, continued use of additional audio playback of other bells from the Kolner Dom (Cologne Cathedral) in a sequential manner (two (2) through eleven (11)) in a sequential manner following the above process.

As an alternate method of treatment, the system 10 provides the ability to produce twelve (12) different and separate musical notes to achieve the same effect, also following the above process. This is achieved by user selection of the twelve-way slide switch 50. Additionally, activation of the switch 60 allows for the twelve (12) musical notes (as selected by the twelve-way slide switch 50, to be played by various different instruments. Such selection of the instruments is obtained in a scrolling manner using repetitive pushes on the switch 60. Volume is actuated by selective control of the volume control 62.

When not being used for relief purposes, the user may listen to their favorite radio broadcast by pushing the radio activation switch 55. At any point in time, and upon depletion of the power level of the power supply 70, the user may recharge the system 10 by use of the USB charging port 75 or replace the batteries. After use of the system 10, it is deactivated and stored until needed again in a repeating and cyclical manner.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A noise injury relief system, comprising:

an enclosure sized for pocket carry and having a front face and a top surface;

a cartridge insertion opening formed in the top surface of the enclosure and configured to receive a vaping cartridge;

an eleven-position mechanical slide switch mounted on the front face;

a twelve-position mechanical slide switch mounted on the front face adjacent the eleven-position mechanical slide switch;

a first internal audio storage module;

a second internal audio storage module;

an instrument-selection switch mounted on the front face;

a volume control knob mounted on the front face;

a main controller electrically coupled to the eleven-position mechanical slide switch, the twelve-position mechanical slide switch, the instrument-selection switch, and the volume control knob;

a signal generator electrically coupled downstream of the main controller; and, a wireless transmitter electrically coupled to the signal generator, and, wherein the eleven-position mechanical slide switch is configured to generate eleven discrete selection signals corresponding to eleven internally stored audio recordings;

wherein the twelve-position mechanical slide switch is configured to generate twelve discrete selection signals corresponding to twelve internally stored musical notes;

wherein the first internal audio storage module stores the eleven internally stored audio recordings corresponding to the eleven discrete selection signals;

wherein the second internal audio storage module stores the twelve internally stored musical notes corresponding to the twelve discrete selection signals;

wherein the instrument-selection switch is configured to modify playback characteristics of the twelve internally stored musical notes without altering the eleven internally stored audio recordings;

wherein the main controller is configured to select audio content from the first internal audio storage module or the second internal audio storage module in response to physical actuation of the eleven-position mechanical slide switch or the twelve-position mechanical slide switch, respectively;

wherein audio output selected by the main controller is passed through the signal generator prior to being transmitted by the wireless transmitter; and, wherein the eleven-position mechanical slide switch, the twelve-position mechanical slide switch, the instrument-selection switch, and the volume control knob are dedicated physical controls provided on the front face of the enclosure.

2. The noise injury relief system of claim 1, wherein the enclosure has dimensions of two and one-half inches in width, five inches in height, and three-eighths of an inch in thickness;

wherein the enclosure includes rounded corners configured to facilitate insertion and removal of the noise injury relief system from a clothing pocket; and, wherein the wireless transmitter is a Bluetooth transmitter configured to transmit the audio output to a wireless audio device for private playback.

* * * * *